United States Patent
Peng et al.

(10) Patent No.: US 8,110,410 B2
(45) Date of Patent: Feb. 7, 2012

(54) NANOFLUDIC FIELD EFFECT TRANSISTOR BASED ON SURFACE CHARGE MODULATED NANOCHANNEL

(75) Inventors: Hongbo Peng, Yorktown Heights, NY (US); Stanislav Polonsky, Yorktown Heights, NY (US); Stephen M. Rossnagel, Yorktown Heights, NY (US); Gustavo Alejandro Stolovitzky, Yorktown Heights, NY (US)

(73) Assignee: International Business Machines Corporation, Armonk, NY (US)

( * ) Notice: Subject to any disclaimer, the term of this patent is extended or adjusted under 35 U.S.C. 154(b) by 177 days.

(21) Appl. No.: 12/493,811

(22) Filed: Jun. 29, 2009

(65) Prior Publication Data

US 2010/0327255 A1    Dec. 30, 2010

(51) Int. Cl.
*H01L 21/00* (2006.01)
(52) U.S. Cl. .......... 438/1; 257/9; 257/E51.005; 977/938
(58) Field of Classification Search .......... 438/1; 257/9; 257/E51.005; 977/938
See application file for complete search history.

(56) References Cited

U.S. PATENT DOCUMENTS

| | | |
|---|---|---|
| 2003/0226604 A1 | 12/2003 | Schlautmann |
| 2004/0007740 A1* | 1/2004 | Abstreiter et al. ............ 257/347 |
| 2007/0231211 A1* | 10/2007 | Yoo et al. ........................ 422/88 |
| 2007/0286773 A1 | 12/2007 | Schlautmann |
| 2008/0185057 A1 | 8/2008 | Prakash et al. |

OTHER PUBLICATIONS

Ion Transport in Nanofluidic Channels, Hirofumi Daiguji, Peidong Yang, and Arun Majumdar, Nano Letters 2004 vol. 4, No. pp. 137-142.
Electrokinetic Flow Control in Microfluidic Chips, K.. Horiuchi et al., Journal: Lab On a Chip, Jun. 2006, pp. 714-723.

* cited by examiner

*Primary Examiner* — Bradley K Smith
*Assistant Examiner* — Mohammad T Karimy
(74) *Attorney, Agent, or Firm* — Michael J. Buchenhorner; Vazken Alexanian (57) ABSTRACT

A field effect transistor device includes: a reservoir bifurcated by a membrane of three layers: two electrically insulating layers; and an electrically conductive gate between the two insulating layers. The gate has a surface charge polarity different from at least one of the insulating layers. A nanochannel runs through the membrane, connecting both parts of the reservoir. The device further includes: an ionic solution filling the reservoir and the nanochannel; a drain electrode; a source electrode; and voltages applied to the electrodes (a voltage between the source and drain electrodes and a voltage on the gate) for turning on an ionic current through the ionic channel wherein the voltage on the gate gates the transportation of ions through the ionic channel.

11 Claims, 7 Drawing Sheets

Partition the reservoir with a membrane of at least two electrically insulating layers and an electrically conductive gate.

510

⇩

Open a nanochannel through the membrane.

520

⇩

Fill the reservoir through the nanochannel with an ionic solution to produce a surface-charged modulated ionic channel.

530

⇩

Add source and drain electrodes.

540

⇩

Apply a voltage to the gate to turn on an ionic current.

550

⇩

Measure ionic current through the nanochannel.

560

NANOFLUDIC FIELD EFFECT TRANSISTOR BASED ON SURFACE CHARGE MODULATED NANOCHANNEL

CROSS-REFERENCE TO RELATED APPLICATIONS

None.

STATEMENT REGARDING FEDERALLY SPONSORED-RESEARCH OR DEVELOPMENT

None.

INCORPORATION BY REFERENCE OF MATERIAL SUBMITTED ON A COMPACT DISC

None.

FIELD OF THE INVENTION

The invention disclosed broadly relates to the field of field effect transistors and more particularly relates to the field of nanofluidic field effect transistors. The invention also relates to the field of manipulating bio-molecules in a solution by controlling the passage of ions/charged molecules through a nanochannel filled with an ionic solution.

BACKGROUND OF THE INVENTION

Many methods have been explored for regulating ionic current. Recently, experimental demonstrations have shown that the ionic current through a uniformly surface-charged ionic channel can be modulated by the gate voltage applied on the channel. However, due to the native surface charge on the walls of the channel, the design requires high gate voltages and it is very difficult to completely turn off the ionic current. A "bipolar" ionic transistor by chemically modulating the surface charge of the nanochannel. It was demonstrated that the ionic current was completely off in this bipolar ionic transistor. But this bipolar ionic transistor is a "passive" transistor, with no active electrical gate control.

A need exists for an electrical gate on a surface-charge modulated ionic channel, wherein by applying a gate voltage on the electrical gate, one can turn on the ionic current.

SUMMARY OF THE INVENTION

Briefly, according to an embodiment of the invention a field effect transistor is based on a surface-charge-modulated nanofluidic channel filled with ionic solution. The nanofluidic field effect transistor (FET) includes the following: a reservoir formed of an electrically insulating material that is separated into two parts by a membrane. The membrane includes three layers: two electrically insulating layers and one electrically conductive gate layer disposed between the two electrically insulating layers. The gate layer has a surface charge with a polarity that is different from that of the surface charge of at least one of the two electrically insulating layers. The nanofluidic FET further includes a nanochannel introduced through the membrane that connects the two parts of the reservoir.

An ionic channel is produced with the introduction of an ionic solution through the nanochannel, filling the reservoir. Also included are a drain electrode and a source electrode for facilitating an ionic current, which is 0 when there is no voltage bias applied on the gate layer due to the modulation of the surface charge inside the nanochannel. A voltage is then applied to the gate to turn on the ionic current through the ionic channel, gating the transportation of ions through the ionic channel. The ionic current that is produced can be easily measured through the nanochannel.

According to an embodiment of the present invention, a method for producing a nanofluidic FET includes steps or acts of: bifurcating a reservoir with a membrane disposed between the two parts and the membrane is made of three layers: two electrically insulating layers and one electrically conductive gate layer disposed between the two electrically insulating layers; producing a nanochannel opening through the membrane; filling the reservoir by dispensing an ionic solution into the nanochannel made of different surfaces to produce a surface-charged modulated ionic channel; adding source and drain electrodes; applying a bias voltage between the source and drain electrodes and applying gate voltage on the gate layer in the membrane; and measuring the ionic current through the nanochannel.

BRIEF DESCRIPTION OF THE DRAWINGS

To describe the foregoing and other exemplary purposes, aspects, and advantages, we use the following detailed description of an exemplary embodiment of the invention with reference to the drawings, in which.

While the invention as claimed can be modified into alternative forms, specific embodiments thereof are shown by way of example in the drawings and will herein be described in detail. It should be understood, however, that the drawings and detailed description thereto are not intended to limit the invention to the particular form disclosed, but on the contrary, the intention is to cover all modifications, equivalents and alternatives falling within the scope of the present invention.

DETAILED DESCRIPTION

We discuss a field effect transistor (FET) based on a nanofluidic channel filled with an ionic solution to which we add an electrical gate on the surface-charged modulated ionic channel, to produce a modulated surface-charged nano-fluidic field effect transistor. Due to the modulation of the surface charge inside the nanochannel, the transportation of ions through the nanochannel is interrupted when gate voltage is off. By applying a gate voltage on the electrical gate, one can turn on the ionic current through the nanochannel.

Since the carriers are ions and the mobility of ions is dependent on the ion species and the solvent used, this invention can be applied as a chemical sensor (both ions and solvent). From the ionic current and the turn-on gate voltage, one can tell the species of the ions and also the solvent because the ionic current is dependent on the interactions between the ions and the solvent. In this manner one can identify the ions passing through the channel if the solvent is known; or identify the solvent if the ion is known.

This is a "fluidic" alternative to a MOSFET (metal-oxide semiconductor field-effect transistor). In another embodiment of the present invention, the ions can be macro ions, such as charged biomolecules (DNA or proteins) or charged polymers. In such an embodiment, we are able to control the passage of biomolecules through the nanochannel. Just like a Si MOSFET can be used as a unit in analog/digital logic circuits, this fluidic alternative to MOSFET can also be used as a unit for analog/digital logic circuits.

To build this device, one can use non-Si substrates, such as injection molded plastics, as a "low cost" alternative to Si MOSFET. The diameter of the ionic channel can be smaller than 2 nm, and the physics of ionic conductivity could be very different from that in a continuous medium. So it is possible that the speed of this "fluidic" MOSFET alternative is faster than extrapolations of a larger continuum design might suggest. Compared to Si MOSFET, this "fluidic" MOSFET alternative has the following advantage: it enables control of the passage of charged ions through a nanopore/nanochannel.

Figure 1:
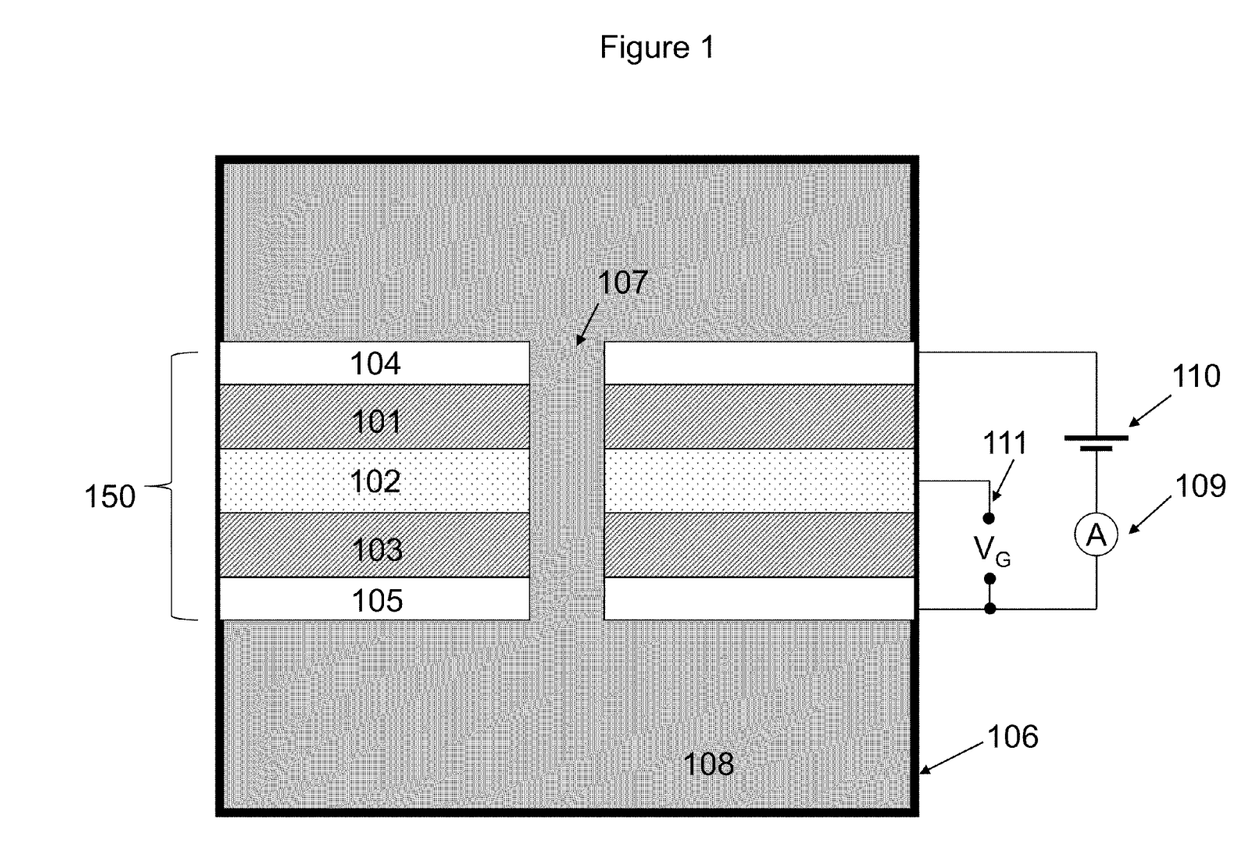
FIG. 1 shows a cross-section of the nanofluidic field effect transistor, according to an embodiment of the present invention.

With reference now to the figures and in particular with reference to FIG. 1, we show a cross-section of a nanofluidic field effect transistor, according to an embodiment of the present invention. A membrane 150 is made of layers (electrodes and dielectrics) 101, 102, 103, 104 and 105 and partitions reservoir 106 into two parts. The reservoir 106 is preferably made of any electrically insulating material such as a non-silicon substrate.

A nanometer size hole 107 is made through the membrane 150. The hole 107 can be made by focused electron beam drilling, focused ion beam milling, reactive ion etching or any other practicable method that is known or envisioned. The reservoir 106 and the hole 107 are then filled with an ionic buffer 108 such as water or other solvents.

Figure 2A:
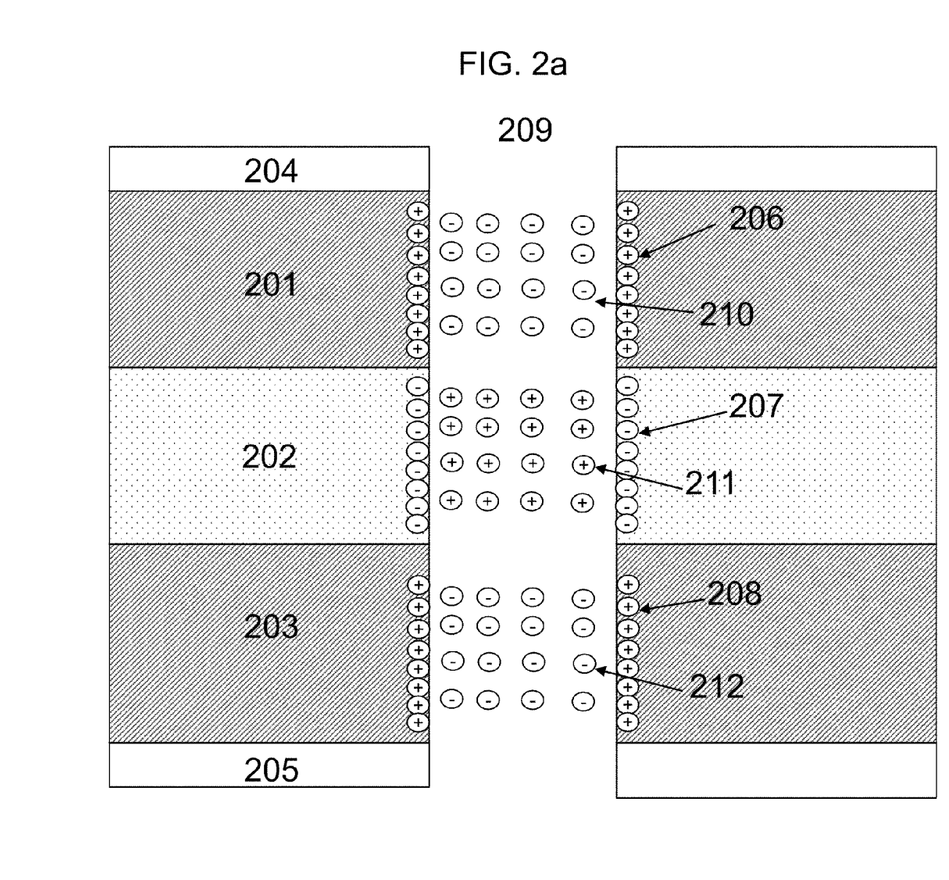
FIG. 2a shows the schematic of the charge distribution in the nanofluidic field effect transistor at zero gate voltage, according to an embodiment of the present invention.
Figure 4:
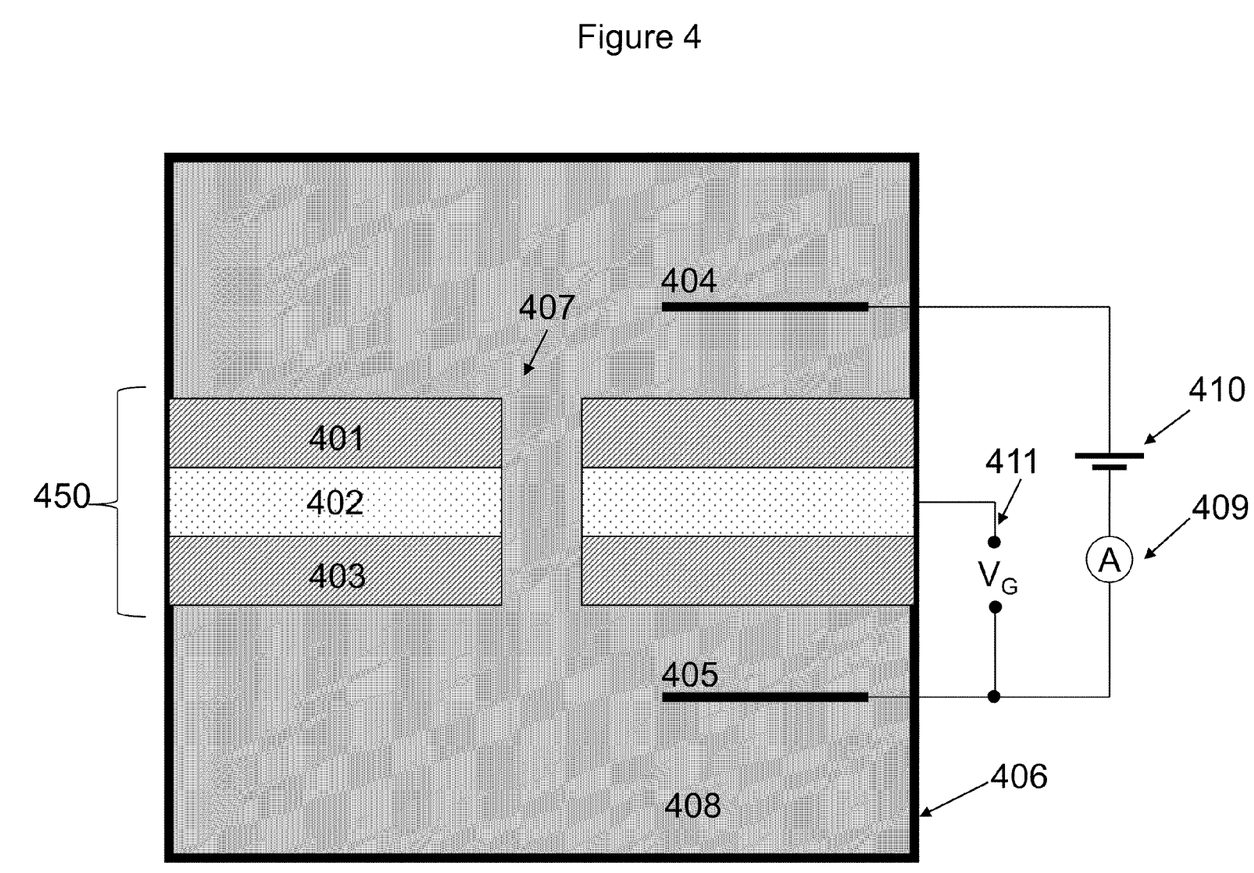
FIG. 4 shows the cross-section of the nanofluidic field effect transistor with the minimum essential parts in the membrane.

Although FIG. 1 shows the membrane 150 with five layers, it should be noted that the membrane 150 is not limited to those layers shown in FIG. 1. Other combinations of layers are possible; the requirement being that at least three layers must be present (as shown in FIG. 4). The three essential layers of the membrane are: an electrically conductive gate layer 102 and two electrically insulating layers 101 and 103 with the gate layer 102 sandwiched between the two electrically insulating layers 101 and 103. It is essential that the gate layer 102 have a different surface charge polarity from at least one of the two electrically insulating layers. In the exemplary embodiment of FIG. 1, assume that gate layer 102 has a negative surface charge; layer 101 has a positive surface charge; and the surface of layer 103 has a positive charge as shown in FIG. 2a (layer 103 could also be not charged as a passivation layer, as shown in FIG. 2c). The key element of the embodiments is to use electrical gate/gate voltage to change the surface properties of the gate layer 102, to regulate the ionic current flow at certain gate voltages. The surface charge that is critical is the charge on the surfaces of the electrode/insulating layers that are on the inside of the nanochannel 107 and touches the ionic solution 108. Note that in FIG. 1, in the case that the surface of 103 is also positively charged as that of 101, the performance of the device is better.

Additional components of the nanofluidic FET are the source and drain electrodes 104 and 105 for ionic current. These electrodes can be separated from the membrane 150 and dipped anywhere in the ionic solution 107 because the ionic solution 107 is a good conductor. The gate voltage 111 applied on membrane parts 102 and 105 can then modulate the ionic current 109.

Note that in addition to the five layers shown here, an additional pair of outer electrodes can be added to serve as top and bottom guard electrodes to reduce any impact of an external electrolyte potential.

For membrane part 102, it needs to be electrically conductive except for the surface in contact with the ionic buffer 108 (the surface can be either electrically conductive or electrically non-conductive), so one can also put an insulating coating layer on the surface of the membrane part 102 that abuts the nanochannel. The surface charge is dependent on both the surface material and pH of the ionic buffer. So as long as films 101, 103 are made of materials different from that of film 102, one can find a certain pH range that the surface charges of 101, 103 have a different sign from that of film 102. For example, membrane part 101 and 103 could be $Si_3N_4$ films and membrane part 102 could be doped amorphous Si followed by thermal oxidization of the surface ($SiO_2$).

At a pH value between 4 and 6.4, $SiO_2$ is negatively surface-charged while $Si_3N_4$ is positively surface-charged. Membrane parts 104 and 105 could be made of any material for electrochemical electrodes, such as Ag/AgCl electrodes and Pt electrodes.

The ionic buffer 108 can be any ionic solution, such as KCl (potassium chloride) solution, which satisfies the following two conditions: (1) the ionic concentration is low enough that the Debye length of the ionic solution is comparable with the diameter of the hole/nanochannel 107; (2) it is at certain pH value so that the surface charges of 101, 103 have different polarity from that of film 102.

FIG. 2a shows the schematic of the charge distribution in the nanofluidic field effect transistor at zero gate voltage. Charges 201, 202, 203, 204, 205 correspond to the membrane parts 101, 102, 103, 104, 105 in FIG. 1, respectively. Charges 206, 207, 208 are surface charges on membrane parts 201, 202, 203 respectively. Charges 206 and 208 are positive charges and 207 are negative charges. Charges 208 and 212 are for the case that 103/203 is positively charged. As there is an ionic buffer in the nanochannel 209, there will be counter-ions 210, 211, 212 near the charged surface to form an electrical double layer.

Figure 2B:
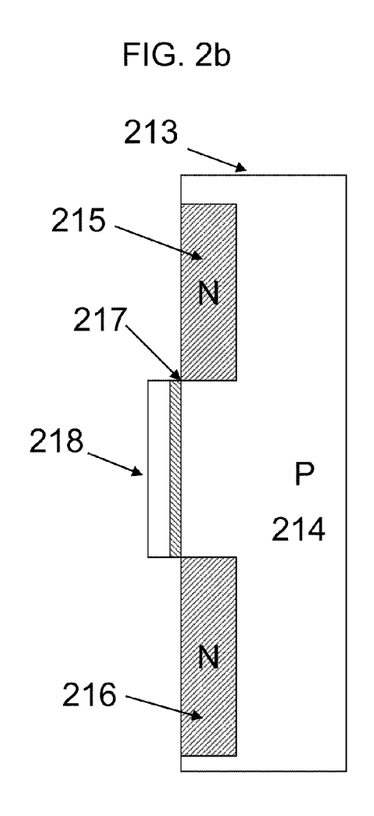
FIG. 2b shows a MOSFET with a p-type substrate, according to the known art.
Figure 2C:
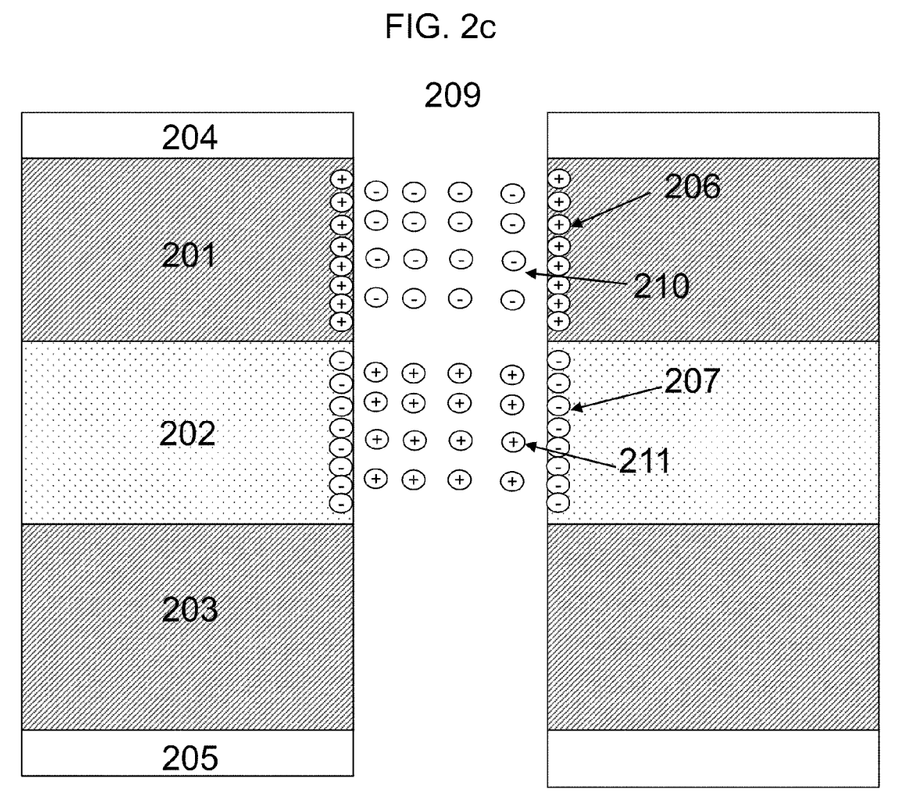
FIG. 2c shows a schematic similar to FIG. 2a with an uncharged passivation layer, according to an embodiment of the present invention.

Assuming that part 103/203 is positively charged, the diameter of the nanochannel 209 is smaller than twice of the thickness of the electrical double layer, the entire nanochannel will be patterned with negative and positive counter-ions (net charge or space charge in the language of semiconductor), forming a structure similar to the MOSFET 213 shown in FIG. 2b where 214 is a p-type substrate, 215 and 216 are n-doped source and drain areas, 217 is the oxide and 218 is the metal gate. As mentioned previously, the part 103/203 can also be uncharged, as shown in FIG. 2c, although the performance is not that much better than as shown in FIG. 2a.

The diameter of the nanochanel 209 can be smaller than 2 nm, but there is no need to be that small. The diameter is preferably smaller than twice the Debye length, which could range from 0.3 nm (1 M ionic solution) to 10 nm (0.001 M ionic concentration) depending on the ionic strength of the ionic solution.

The ionic current between electrodes 204 and 205 through the nanochannel 209 is zero or very small at this zero gate voltage. The structure of FIG. 2a differs from the MOSFET 213 of FIG. 2b in that the nanofluidic field effect transistor is based on controlling the motion of ions through ionic solutions while the MOSFET 213 is based on controlling the motion of electrons or holes through the lattice of solid state materials. As stated earlier, the ions in the nanofluidic FET can also be macro ions or charged biomoleclues, such as DNAs, RNAs, proteins, and so forth, allowing us to control the passage of charged biomolecules through a nanopore/nanochannel.

FIG. 3a shows the schematic of the charge distribution in the nanofluidic field effect the transistor at a certain gate voltage. Films 301, 302, 303, 304, 305 correspond to the membrane parts 101, 102, 103, 104, 105 in FIG. 1 respectively. Charges 306, 307, 308 are surface charges on membrane part 301, 302, 303 respectively. Charges 306 and 308 are positive charges and 307 are negative charges. Inside the nanochannel 309, there are counter-ions 310, 311, 312. Charges 308 and 312 are for the case that the surface of 103 is positively charged. FIG. 2a illustrates that case.

If one applies a voltage on gate 302, the associated counter-ions 311 will be redistributed. In the case shown here, a positive gate voltage will attract more negative ions into the region enclosed by 302 and drive some positive counter-ions 311 out of the region enclosed by 302. This will form a "charge inversion" area 313, which has no net charge or has net negative ions. The area 313 will turn on the ionic current between electrodes 304 and 305. As shown in FIG. 3c, it is also possible that the voltage on gate 302 can change the polarity of the surface charge 307 from negative to positive and accordingly all the counter-ions 311 will be all negative-charged. In this case, it will also turn on the ionic current between electrodes 304 and 305.

Figure 3:
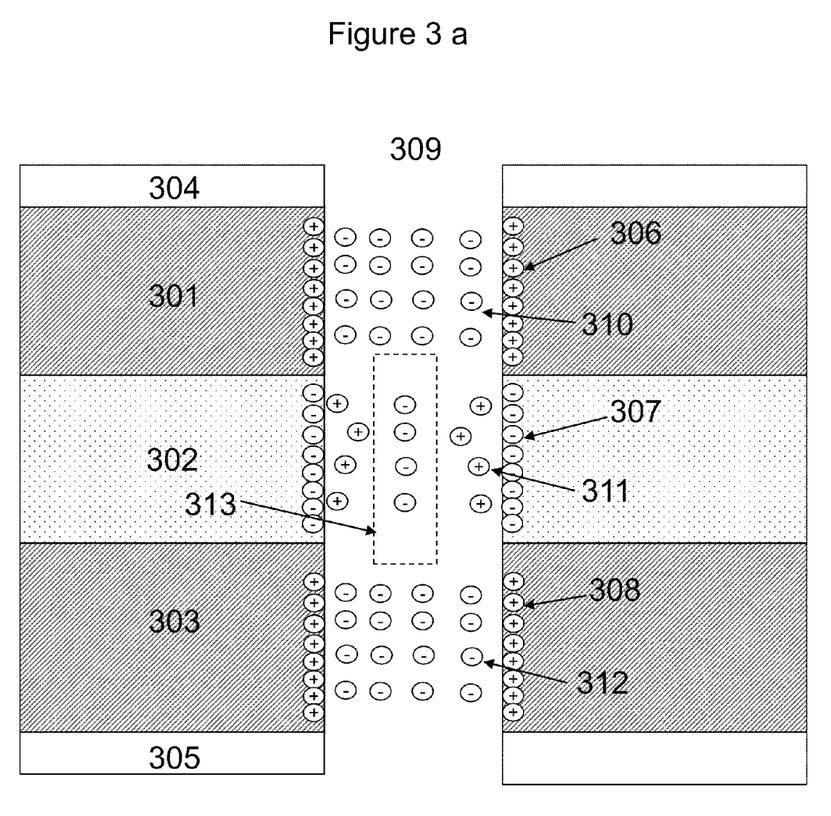
FIG. 3a shows the schematic of the charge distribution in the nanofluidic field effect the transistor at a certain gate voltage, according to an embodiment of the present invention.
FIG. 3b shows the schematic of FIG. 3a with all of the counter-ions negatively charged, according to an embodiment of the present invention.

FIG. 4 shows the schematic of the nanofluidic field effect transistor with the three essential parts in the membrane 450, which is made of layers 401, 402 and 403 (partitioning the reservoir 406 into two parts). In this embodiment, source and drain electrodes 404 and 405 are dipped in the ionic buffer 408. A nanometer size hole 407 is made through the membrane 450 by focused electron beam drilling, focused ion beam milling, reactive ion etching or other methods. The reservoir 406 and the hole 407 are then filled with an ionic buffer 408 such as water or another solvent. Electrodes 404 and 405 are electrodes for measuring ionic current 409 through the hole/nanochannel 407 when a voltage bias 410 is applied on the electrodes. The gate voltage 411 applied between membrane parts 402 and 405 can then modulate the ionic current 409 through the hole 407. The principle of turning on the ionic current is the same as shown in FIGS. 2 and 3. The only difference is that the electrodes 304 and 405 are dipped in the ionic buffer.

Membrane parts 401 and 403 are made of any electrically insulating material while membrane part 402 is made of any electrically conductive material. For membrane part 402, one can also put an insulating coating layer on its surface in the nanochannel 407. On the surface that is in contact with the ionic buffer 408, at least one of the membrane parts 401 and 403 has a surface charge of a different polarity than the membrane part 402.

Electrodes 404 and 405 could be made of any material for electrochemical electrodes, such as Ag/AgCl electrodes and Pt electrodes. For the ionic buffer 408, it can be any ionic solution, such as KCl (potassium chloride) solution, which satisfies the following two conditions: (1) the ionic concentration is low enough that the Debye length is comparable with the diameter of the hole/nanochannel 407; and (2) it is at a certain pH value so that the surface charges of at least one of the two films 401, 403 has different polarity from that of film 402.

Figure 5:
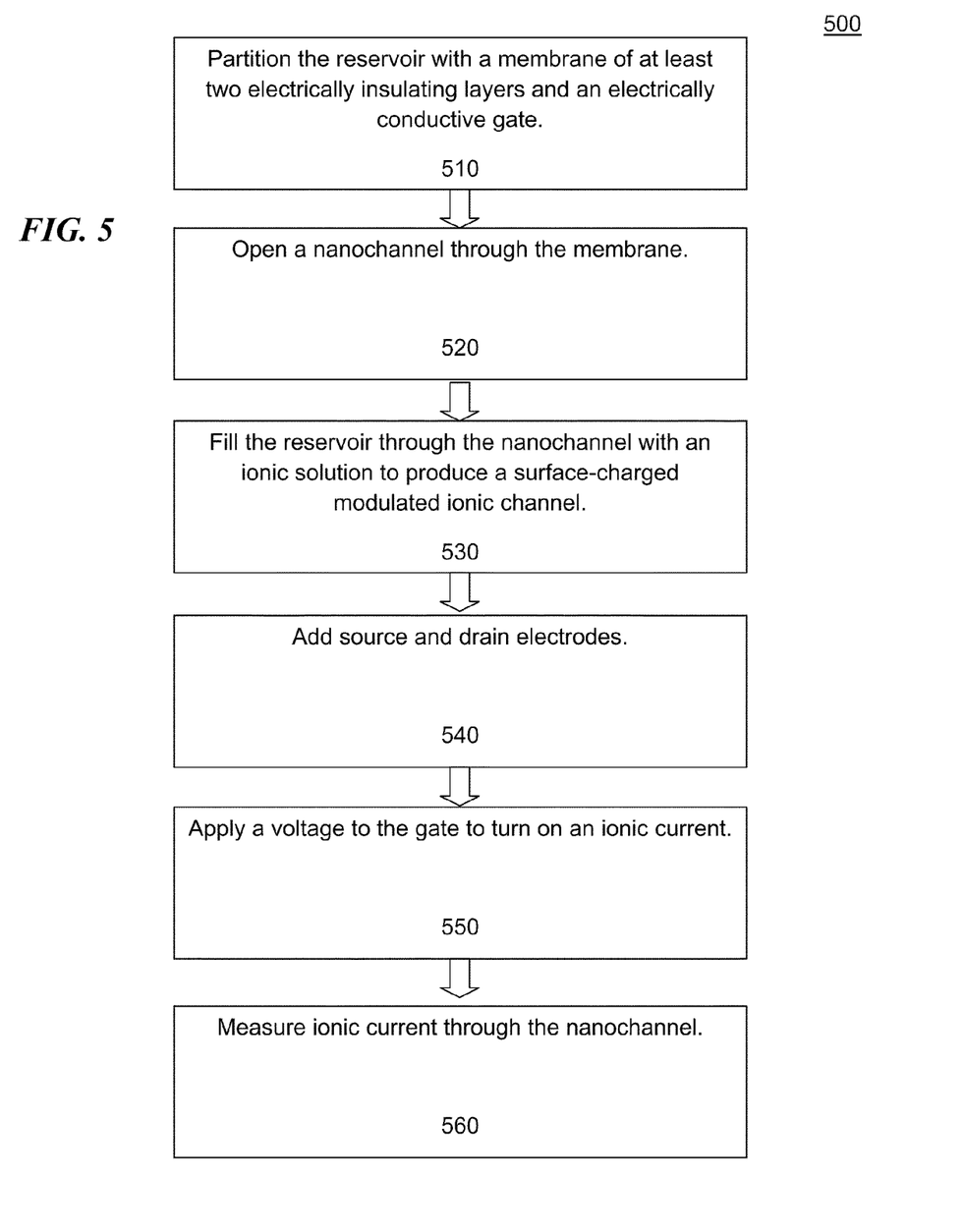
FIG. 5 is a flow diagram of a method for producing a nanofluidic field effect transistor, according to an embodiment of the present invention.

Referring now to FIG. 5, we show a flow diagram 500 of the steps for producing the nanofluidic FET as has been described. First, at step 510, beginning with an insulating material to form a reservoir, we partition the reservoir with a membrane of at least three layers. One of the layers must be an electrically conductive gate sandwiched between two electrically insulating layers.

To produce the modulating effect, the gate layer must have a surface charge that is different than the surface charge of at least one of the electrically insulating layers. As an example, the gate could be formed from doped amorphous silicon followed by thermal oxidation of the surface to produce silicon dioxide; while the two layers could be formed of silicon nitride. The desired effect in polarizing the layers is to achieve a pH range with a different surface charge polarity in contiguous layers.

In step 520 a hole is opened through the membrane. This nano-sized hole is a nanochannel or nanopore through which an ionic solution is applied in step 530. The ionic solution can be water or potassium chloride. The ionic solution fills the nanochannel and the reservoir. The membrane layers of different surface properties transform the nanochannel to a surface-charged modulated ionic channel when interacting with ions such as $H^+$ and $OH^-$, in the solution. The surface charge emanates from the interactions between the surface and ions such as $H^+$ and $OH^-$ or other similar ions in solution. So different surface properties will generate different surface charge polarities, which are also tunable by the pH of the ionic solution.

In step 540 the source and drain electrodes are introduced and voltage bias is applied between them. These electrodes can be dipped into the ionic solution as shown in FIG. 4; or, in the alternative, they can be layered on the membrane as shown in FIG. 1. The source and drain electrodes can be any electrochemical electrodes, such as silver/silver chloride or platinum.

In step 550 we turn on an ionic current by applying voltage to the gate. The cause of ionic current is due to the voltage bias applied on source and drain electrodes. Gate voltage simply allows that happen. This allows the transportation of ions through the surface-charge-modulated nanopore/nanochannel. At this point we are able to measure the ionic current through the nanochannel. A regular ampmeter can be used to measure the ionic current because it is converted to regular current at the source and drain electrodes. Turning off the voltage halts the movement of the ions through the nanopore/nanochannel.

Therefore, while there has been described what is presently considered to be the preferred embodiment, it will be understood by those skilled in the art that other modifications can be made within the spirit of the invention. The above descriptions of embodiments are not intended to be exhaustive or limiting in scope. The embodiments, as described, were chosen in order to explain the principles of the invention, show its practical application, and enable those with ordinary skill in the art to understand how to make and use the invention. It should be understood that the invention is not limited to the embodiments described above, but rather should be interpreted within the full meaning and scope of the appended claims.

We claim:

1. A method for producing a nanofluidic field effect transistor, said method comprising:

bifurcating a reservoir into two parts with a membrane disposed between the two parts, said membrane comprising three layers:
two electrically insulating layers; and
an electrically conductive gate disposed between two electrically insulating layers, wherein said electrically conductive gate comprises a surface charge polarity different from at least one of the two electrically insulating layers when they are in contact with an ionic solution;
producing a nanochannel opening through the membrane;
filling the reservoir by dispensing an ionic solution through the nanochannel opening to produce a surface-charge-modulated ionic channel, wherein the modulated surface charge is due to different surface properties of the two electrically insulating layers and the electrically conductive gate;
adding source and drain electrodes;
forming an ionic buffer in the nanochannel, causing counter-ions near a charged surface to form an electrical double layer;
applying a bias voltage between the source and drain electrodes and a voltage on the electrically conductive gate layer in the membrane to turn on an ionic current and gating the transportation of ions through the nanochannel; and
measuring ionic current through the nanochannel opening, said nanochannel opening having a diameter smaller than twice a thickness of the electrical double layer, wherein an entirety of the nanochannel is patterned with negative and positive counter-ions.

2. The method of claim 1 further comprising applying an insulating coating layer on a surface of the electrically conducting gate that abuts the nanochannel.

3. The method of claim 1 further comprising a step of:
turning off the bias voltage to turn off the ionic current.

4. The method of claim 1 wherein filling the reservoir comprises filling the reservoir with macro ions.

5. The method of claim 4 comprising filling the reservoir with solution of charged biomolecules.

6. The method of claim 1 wherein producing the nanochannel comprises applying focused electron beam drilling.

7. The method of claim 1 wherein producing the nanochannel comprises applying focused ion beam milling.

8. The method of claim 1 wherein producing the nanochannel comprises producing the nanochannel with a diameter less than twice a Debye length of the ionic solution.

9. The method of claim 1 wherein the step of adding the drain and source electrodes comprises dipping said source and drain electrodes in the ionic solution.

10. The method of claim 1 wherein the step of adding the drain and source electrodes comprises adding them as layers of the membrane, such as two electrically conducting layers.

11. A method for producing a nanofluidic field effect transistor, said method comprising:
bifurcating a reservoir into two parts with a membrane disposed between the two parts, said membrane comprising three layers:
two electrically insulating layers; and
an electrically conductive gate disposed between the two electrically insulating layers, wherein said electrically conductive gate comprises a surface charge polarity different from at least one of the two electrically insulating layers when they are in contact with an ionic solution;
producing a nanochannel opening through the membrane;
filling the reservoir by dispensing an ionic solution through the nanochannel opening to produce a surface-charge-modulated ionic channel, wherein the modulated surface charge is due to different surface properties of the two electrically insulating layers and the electrically conductive gate;
adding source and drain electrodes;
applying a bias voltage between the source and drain electrodes;
applying a voltage on the electrically conductive gate layer in the membrane to turn on an ionic current and gating the transportation of ions through the nanochannel; and
measuring ionic current through the nanochannel;
wherein the nanochannel opening has a diameter smaller than twice the Debye length of the ionic solution, which ranges from 0.3 nm to 10 nm, depending on ionic strength of said ionic solution.

* * * * *